United States Patent
Loftin et al.

(10) Patent No.: US 7,092,762 B1
(45) Date of Patent: Aug. 15, 2006

(54) LOW-POWER, HIGH-MODULATION-INDEX AMPLIFIER FOR USE IN BATTERY-POWERED DEVICE

(75) Inventors: Scott M Loftin, Simi Valley, CA (US); Kelly H McClure, Simi Valley, CA (US)

(73) Assignee: Advanced Bionics Corporation, Valencia, CA (US)

(*) Notice: Subject to any disclaimer, the term of this patent is extended or adjusted under 35 U.S.C. 154(b) by 613 days.

(21) Appl. No.: 10/445,121

(22) Filed: May 23, 2003

Related U.S. Application Data

(62) Division of application No. 09/945,303, filed on Aug. 31, 2001, now Pat. No. 6,591,139.

(60) Provisional application No. 60/230,399, filed on Sep. 6, 2000.

(51) Int. Cl.
  *A61N 1/02* (2006.01)
  *H04B 5/00* (2006.01)

(52) U.S. Cl. .................. 607/60; 607/156; 607/32; 128/903; 128/902

(58) Field of Classification Search .............. 607/60, 607/32, 156, 61; 128/902, 903; 340/870.01; 455/41.1, 41.2
  See application file for complete search history.

(56) References Cited

U.S. PATENT DOCUMENTS

| | | | |
|---|---|---|---|
| 4,223,679 A | 9/1980 | Schulman et al. | |
| 4,441,210 A * | 4/1984 | Hochmair et al. | ......... 455/41.1 |
| 4,571,589 A | 2/1986 | Slocum et al. | |
| 5,193,539 A | 3/1993 | Schulman et al. | |
| 5,193,540 A | 3/1993 | Schulman et al. | |
| 5,697,076 A | 12/1997 | Troyk et al. | |
| 5,741,316 A | 4/1998 | Chen et al. | |
| 5,766,232 A | 6/1998 | Grevious et al. | |
| 5,948,006 A | 9/1999 | Mann | |
| 6,047,214 A | 4/2000 | Mueller et al. | |
| 6,073,050 A | 6/2000 | Griffith | |
| 6,099,479 A | 8/2000 | Christopherson et al. | |
| 6,163,721 A | 12/2000 | Thompson | |
| 6,185,452 B1 | 2/2001 | Schulman et al. | |

FOREIGN PATENT DOCUMENTS

| | | |
|---|---|---|
| WO | WO 98/43700 | 8/1998 |
| WO | WO 98/37926 | 9/1998 |
| WO | WO 98/43701 | 10/1998 |

* cited by examiner

*Primary Examiner*—Kennedy Schaetzle
(74) *Attorney, Agent, or Firm*—Bryant R. Gold; Victoria A. Poissant

(57) ABSTRACT

An external transmitter circuit drives an implantable neural stimulator having an implanted coil from a primary coil driven by a power amplifier. For efficient power consumption, the transmitter output circuit (which includes the primary coil driven by the power amplifier inductively coupled with the implanted coil) operates as a tuned resonant circuit. When operating as a tuned resonant circuit, it is difficult to modulate the carrier signal with data having sharp rise and fall times without using a high power modulation amplifier. Sharp rise and fall times are needed in order to ensure reliable data transmission. To overcome this difficulty, the present invention includes an output switch that selectively inserts a resistor in the transmitter output coil circuit in order to de-tune the resonant circuit only during those times when data modulation is needed. Such de-tuning allows sharp rise and fall times in the data modulation without the need for using a high power modulation amplifier. Because data modulation is typically needed for only a small percent of the time that a carrier signal is present, it is thus possible using the present invention to achieve reliable data modulation, transmission and reception without having to use a high power modulation amplifier in the transmitter.

7 Claims, 4 Drawing Sheets

LOW-POWER, HIGH-MODULATION-INDEX AMPLIFIER FOR USE IN BATTERY-POWERED DEVICE

The present application is a Divisional of U.S. application Ser. No. 09/945,303, filed Aug. 31, 2001 now U.S. Pat. No. 6,591,139; which claims the benefit of U.S. Provisional Application Ser. No. 60/230,399, filed Sep. 6, 2000, which applications are incorporated herein by reference.

BACKGROUND OF THE INVENTION

The present invention relates to modulation amplifiers, and more particularly to a low-power, high-modulation-index amplifier suitable for use in battery-powered devices, e.g., an implantable battery-powered medical device.

Modulation is the process of varying some characteristic of one wave in accordance with another wave. In radio broadcasting, for example, some stations use amplitude modulation (AM), while other stations use frequency modulation (FM). In television, the video portion of the program is amplitude modulated and the audio portion is frequency modulation. In other types of transmissions, such as are used with satellite transmissions or transmissions to and from an implantable medical device, some sort of digital modulation is typically employed, e.g., pulse-amplitude, pulse-code, pulse-duration, pulse-frequency, pulse-position, or pulse-time modulation. These types of digital modulation are typically employed to convey binary bit information, e.g., strings of 1's and 0's, arranged in words and bytes.

A class of small implantable medical devices is known in the art that comprises tiny microstimulators and/or sensors. These tiny microstimulators or sensors, which are hereafter referred to as BION™ devices, are described more fully, e.g., in U.S. Pat. Nos. 5,193,539; 5,193,540 and PCT Publications WO 98/37926; WO 98/43700 and WO 98/43701, each of which patents or publications are incorporated herein by reference. Advantageously, the BION devices are generally small enough to be implanted in a minimally invasive manner through the lumen of a needle, or a similar-sized cannula.

It has been discovered that the sharpness (rise time and/or fall time) of the pulsed modulation used with the BION device has a direct affect on the reliability of the operation of the BION device, and more particularly on the ability of the BION device to properly decode and validate commands. Disadvantageously, the sharp rise times and fall times of the pulsed modulation signals needed for reliable operation of a BION-type device have heretofore required the use of high power modulation amplifiers. High power modulation amplifiers, in turn, are not compatible with the low power requirements of an implantable medical device systems, particularly systems that include battery-powered devices. There is thus a need in the art for a low power modulation amplifier having sharp rise/fall times that may be used within an implantable device system, such as a system that uses the BION device described in the referenced patents and patent applications.

SUMMARY OF THE INVENTION

The present invention addresses the above and other needs by providing an external transmitter circuit that drives an implantable BION device, or other implantable neural stimulator, from a primary coil driven by a power amplifier. For efficient power consumption, the transmitter output circuit (which includes the primary coil driven by the power amplifier inductively coupled with an implanted coil included as part of the implantable BION device) operates as a tuned resonant circuit. Disadvantageously, when operating as a tuned resonant circuit, it is difficult to modulate the carrier signal with data having sharp rise and fall times without using a high power modulation amplifier. In order to overcome this difficulty, the present invention includes an output switch that selectively inserts a resistor in the transmitter output coil circuit in order to de-tune the resonant circuit only when data modulation is needed. Such de-tuning allows sharp rise and fall times in the data modulation without the need for using a high power modulation amplifier. Advantageously, because the data modulation is typically needed for only a very small percent of the time that a carrier signal is present, e.g., 2–4%, it is thus possible using the present invention to achieve reliable data modulation, transmission and reception within the implanted BION (or other) neural simulation device without having to use a high power modulation amplifier in the transmitter.

In accordance with one aspect of the invention, there is provided an implantable medical device, such as an implantable neural stimulator, having an implanted coil through which an externally-generated carrier signal, transmitted from an external primary coil, may be inductively received. The carrier signal is modulated with data at a low duty cycle, e.g., 4% or less, in order to transfer control data into the implantable medical device. The carrier signal provides operating power for the implantable device, either directly by continuously supplying operating power, or indirectly by supplying power on an as-needed basis to recharge a rechargeable battery housed within the implantable medical device. The carrier signal, when not modulated with data (which is typically most of the time, e.g., 96% or more), is inductively coupled to the implant coil through a high Q resonant circuit, e.g., a resonant circuit having a Q greater than about 10. The high Q resonant circuit includes the primary coil and the implant coil. Such high Q resonant circuit promotes the efficient transfer of power into the implantable medical device. A switch selectively connects a resistor in circuit relationship with the external coil to de-tune the tuned resonant circuit when the carrier signal is modulated with data (which is typically a very small percent of the time). Such de-tuning advantageously lowers of the Q of the resonant circuit to about four or less, and allows the data modulation to have sharper rise and fall times at lower power transmission levels. The sharper rise and fall times, in turn, allow more reliable data communication to occur with the implantable medical device.

One embodiment of the invention may be characterized as an implantable medical device system comprising: (1) an external power amplifier having a primary coil; (2) an implant device having an implanted coil; (3) means within the power amplifier for generating a carrier signal that is inductively coupled from the primary coil to the implanted coil through a high Q resonant circuit (Q≦10) that includes the primary coil and the implanted coil; (4) means within the power amplifier for modulating the carrier signal with data; (5) a resistor and a switch within the power amplifier, wherein the resistor is connected to the primary coil through the switch, and wherein the resistor, when connected to the primary coil, de-tunes the high Q resonant circuit (Q≦4); and (6) means within the power amplifier for operating the switch to de-tune the resonant circuit when the carrier signal is modulated with data, wherein the de-tuned resonant circuit allows the data modulation of the carrier signal to occur with sharper rise and fall times, which sharper rise and fall times, in turn, are more reliably detected as data within the implant device.

Another embodiment of the invention may be viewed as a low power modulation amplifier that comprises: (1) an amplifier having an output port; (2) a first capacitor (C1) connected between the output port of the amplifier and a voltage reference, e.g., ground; (3) an antenna coil (L1)

connected to the output port of the amplifier through a second capacitor (C2), the second capacitor functioning as a coupling capacitor; (4) a resistor connected to the antenna coil; and (5) a switch (SW1) that switchably connects the resistor in circuit relationship with the antenna coil.

Yet another embodiment of the invention may be characterized as a method of reliably and efficiently transmitting data and power to an implantable medical device from an external power amplifier. The implantable medical device includes an implanted coil. The external power amplifier includes a primary coil. The method includes the steps of: (1) generating a carrier signal in the power amplifier; (2) inductively coupling the carrier signal from the primary coil to the implanted coil through a high Q ($Q \geq 10$) resonant circuit that includes the primary coil and the implanted coil when only power is to be transmitted to the implantable medical device; (3) modulating the carrier signal with data when data is to be transmitted to the implantable medical device; and (4) inductively coupling the modulated carrier signal from the primary coil to the implanted coil through a low Q ($Q \leq 4$) resonant circuit that includes the primary coil and the implanted coil. In a preferred implementation, the low Q circuit is obtained by electrically connecting a resistor to the primary coil so as to detune the high Q resonant circuit so that it becomes a low Q circuit.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
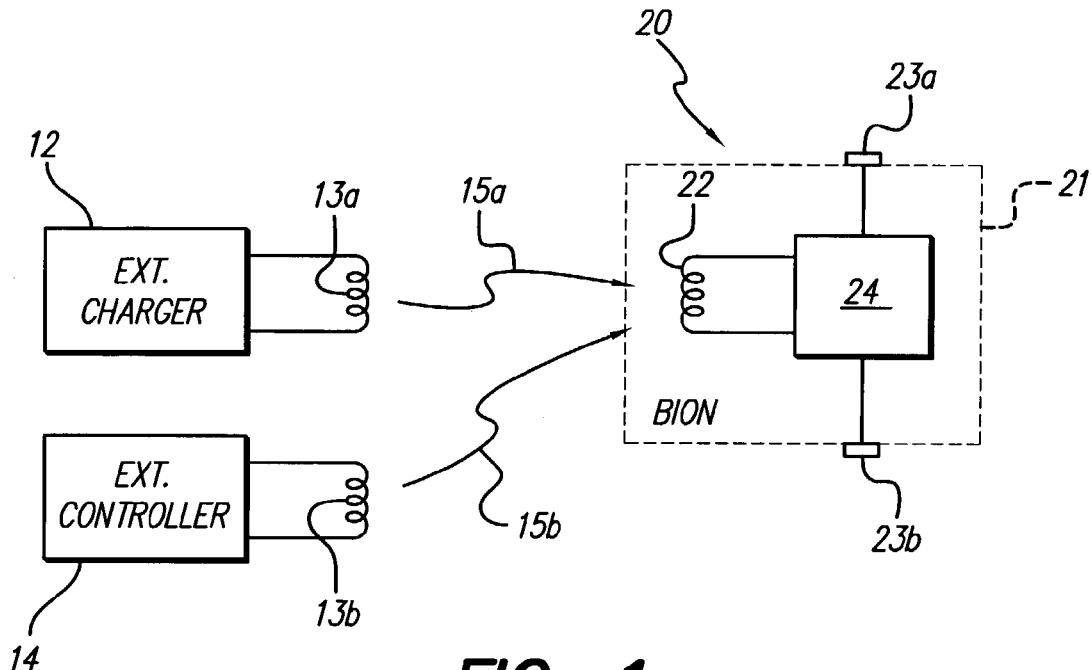
FIG. 1 is a functional block diagram that illustrates the main components of a system that uses an implantable BION-type device.

In order to better understand the present invention, it will first be helpful to provide an overview of an implantable medical device system, e.g., a neural stimulation system, with which the present invention may be used. A functional block diagram that illustrates the main components of such a system is shown in FIG. 1. As seen in FIG. 1, the system includes an implantable BION-type device 20 and one or more external components 12 or 14. The implantable device 20 includes electronic circuitry 24 connected to electrodes 23a and 23b. An implanted coil 22 is also connected to the circuitry 24. All but the electrodes 23a and 23b are housed within an hermetically sealed case 21.

The implantable device 20 interfaces with either an external charger unit 12 and/or an external control unit 14 (also referred to as an "external controller"). The charger unit 12 has a primary coil 13a connected to it. It is through the primary coil 13a that the charger unit electromagnetically couples a carrier signal 15a to the implanted coil 22, and hence to the electrical circuitry 24 included within the device 20. The external controller 14 similarly has a primary coil 13b connected to it through which a carrier signal 15b is coupled to the implanted coil 22 of the implantable device 20.

In operation, either the external charger 12 or the external controller 14 inductively couples a carrier signal 15a or 15b to the implanted coil 22. The implanted circuitry 22 extracts operating power from the carrier signal, e.g., through rectification and filtering. This operating power may be used to directly power the operation of the implantable device 20, e.g., in those instances where the carrier signal is continuously present, or to charge a rechargeable battery (or other power storage element) included within the implantable device 20, e.g., in those instances where the carrier signal is only intermittently present.

In order to control operation of the implantable device 20, the carrier signal is typically modulated with data in some fashion. Such data modulation, when properly detected within the circuitry 24 of the implantable device 20, allows control commands to be sent to the implantable device 20 so that it can better perform its intended function.

The implantable device 20 typically comprises a small neural stimulator having exposed electrodes 23a and 23b through which a small stimulation current pulse is applied to body tissue, e.g., muscles or nerves, in the location where the device 20 is implanted. The implantable device 20 may also comprise a small sensor, e.g., a sensor that senses muscle depolarization or other tissue conditions through the exposed electrodes 23a and 23b; or the implantable device 20 may comprise a combination stimulator/sensor, an implantable pump, a glucose sensor, a chemical sensor, or the like. Significantly, the present invention is not concerned with the implantable device 20 per se. Rather, the present invention is directed to the manner in which a carrier signal may be reliably modulated with data that is coupled to an implantable device 20, regardless of the form or function that the implantable device 20 may take.

Figure 2:
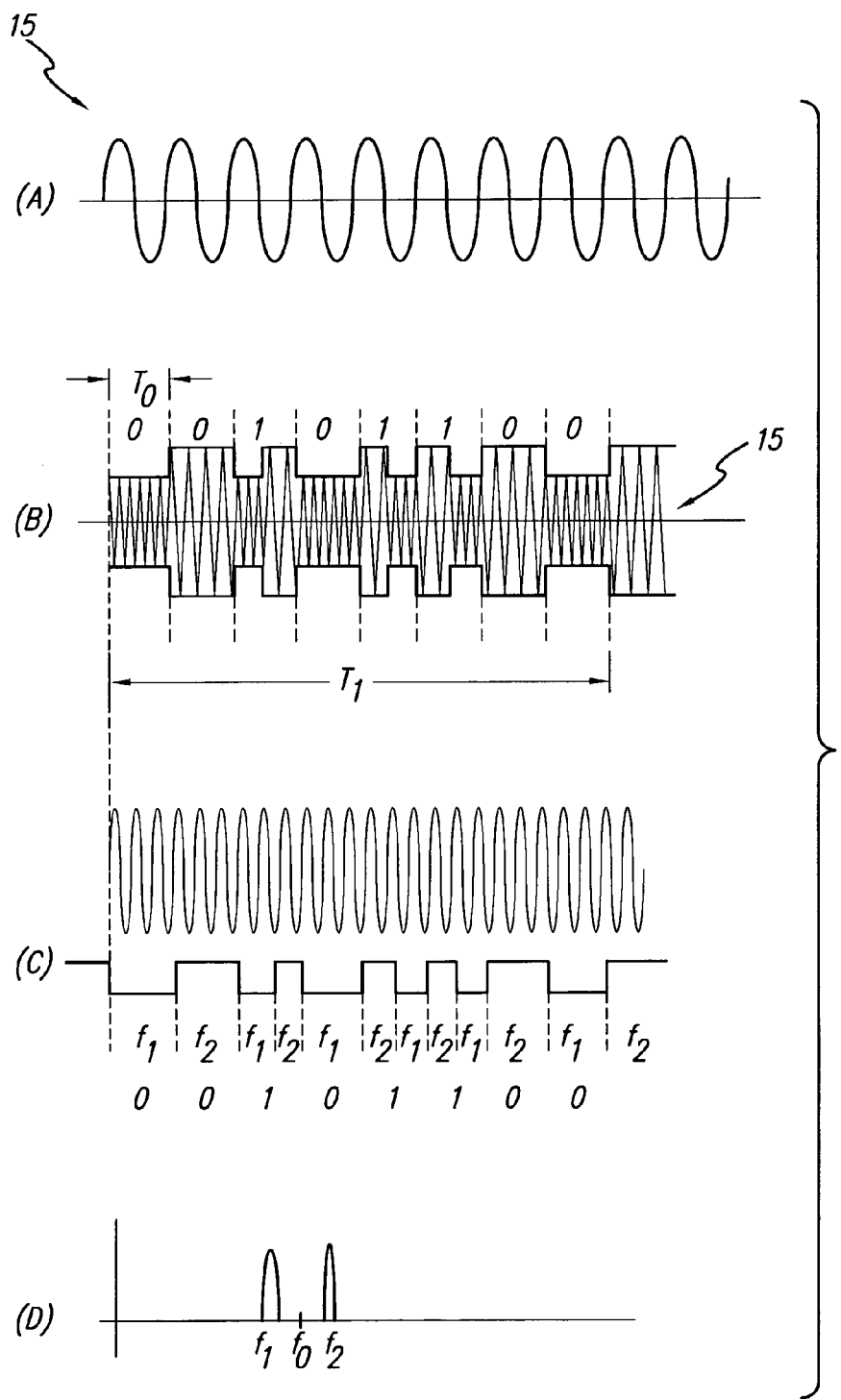
FIG. 2 illustrates various signal and spectra waveforms that may be used with the system of FIG. 1.

FIG. 2 illustrates various signal and spectra waveforms that may be used with the system of FIG. 1. (It should be noted that the time [horizontal] axis shown in FIGS. 2(A) through 2(C) is not necessarily the same.) In FIG. 2(A), the waveform of a typical carrier signal 15 is illustrated. Such carrier signal 15 has a frequency $f_0$ that may vary from a few hundred kilohertz (KHz) to several megahertz (MHZ). For example, in one embodiment, the carrier signal 15a (shown in FIG. 1) generated by the external charger unit 12 has a frequency $f_0$ of 500 KHz; and the carrier signal 15b generated by the external control unit 14 has a frequency $f_0$ of 1.85 MHz.

In FIG. 2(B), a representative carrier signal is illustrated that is amplitude modulated (AM) with a digital data. Any suitable modulation encoding scheme may be used. In FIG. 2(B), by way of illustration, a modified Manchester encoding scheme is employed wherein each bit time T0 is marked by a signal transition, a digital "1" is represented by including a signal transition in the middle of the bit time, and a digital "0" is represented by having no signal transition in the middle of the bit time. Thus, as illustrated in FIG. 2(B), a carrier signal having a frequency $f_0$ is modulated with an eight bit word. The eight bit word has a period of T1, and is made up of individual bit times T1 that comprise "00101100". At least one such eight-bit word, or a series of such words, each having a prescribed digital content, may thus be strung together in order to convey needed control commands to the implant device 20. The data rate of the modulation signal that is applied to the carrier signal may assume any suitable rate, e.g., 10 Hz to 400 KHz. Typically, the data rate will be at least four times slower than the carrier frequency.

In FIG. 2(C), a representative carrier signal is illustrated that is frequency modulated (FM) with digital data. In accordance with such frequency modulation, a carrier frequency of $f_1$, where the frequency $f_1$ is less than the carrier frequency $f_0$, could be used, for example, to represent a digital "0"; and a carrier frequency of $f_2$, where the frequency $f_2$ is greater than the carrier frequency $f_0$, could be used, for example, to represent a digital "1". Other frequency modulation encoding schemes could similarly be used to distinguish a digital "0" from a digital "1". (For example, as with the AM modulation shown in FIG. 2(B), the frequency of the carrier signal shown in FIG. 2(C) could be switched from f1 to f2, or from f2 to f1, at a data bit boundary. If a digital "0" were assigned to the digital bit, no additional frequency changes would occur during the bit time. If a digital "1" were assigned to the digital bit, an additional frequency change would occur approximately in the middle of the bit time.) Frequency modulation is not readily discernable from a time-domain appearance of the carrier waveform, e.g., as shown in FIG. 2(C). However, assuming frequencies of $f_1$ and $f_2$ are used within the frequency modulated carrier signal, a spectral analysis of the frequency modulated carrier signal, depicted in FIG. 2(D), would show spectral lines at both frequencies $f_1$ and $f_2$.

Figure 3:
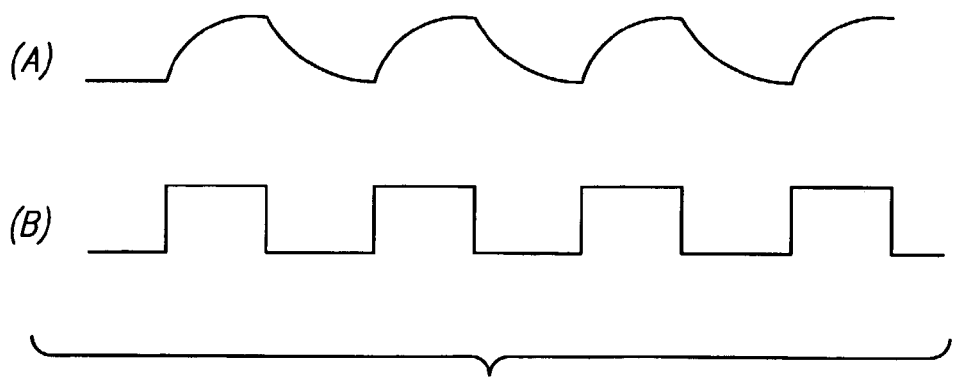
FIG. 3 depicts a data waveform (A) having slow or sluggish rise and fall times, which are generally not compatible with reliable operation of a BION-type stimulation system, and a data waveform (B) having short or sharp rise and fall times, which result from use of the present invention, and which promote the reliable operation of a BION-type stimulation system.

With the foregoing provided as an overview of a typical implanted device system, reference is next made to FIG. 3 where there is shown a data waveform having both slow or sluggish rise and fall times, shown as waveform (A), and a data waveform having short or sharp rise and fall times, shown as data waveform (B). It is noted that the data waveforms depicted in FIG. 3 may be used to provide amplitude modulation or frequency modulation of a carrier signal. The present invention advantageously provides a data modulation signal having sharp rise and fall times, as illustrated in waveform (B) of FIG. 3, which sharp rise and fall times help promote a more reliable data transfer to the implant device 20.

One of the design constraints that must be considered when using an implantable device system as shown in FIG. 1 is the efficient transfer of energy to the implant device 20. In general, the efficient transfer of energy through a primary coil 13a or 13b to an implant coil 22 requires the use of a high Q resonant circuit to couple the two coils. A resonant circuit may be described as one containing both inductance (L) and capacitance (C) in which the capacitive reactance is equal to the inductive reactance. This condition occurs at only one frequency in a circuit with fixed constants, and the circuit is said to be "tuned" to this frequency. The "Q" of a resonant circuit may be defined as a figure of merit of the tuned LC circuit, where Q is generally equal to X/R, where X is the reactance of the circuit, and R is the resistance. Because the resistance in a resonant circuit typically represents an energy loss (the loss occurring due to ohmic heating), a more efficient energy transfer occurs when the resistance is low, or the Q is high. Hence, a preferred circuit for coupling energy between a primary coil and an implanted coil will utilize a resonant circuit having a relatively high Q, e.g., a Q greater than or equal to 10. A Q value of twenty or higher is preferred.

When a high Q circuit is used to couple energy between a primary coil and an implanted coil, the high Q properties of the circuit make it difficult to perform rapid modulation of the carrier signal. Hence, any data modulation signal that also must pass through the high Q resonant circuit tends to exhibit very slow rise and fall times. Disadvantageously, in the context of an implanted medical device system, such as the system shown in FIG. 1, the integrity of the data transmission (i.e., the ability of the system to reliably detect the data that is transmitted) is significantly adversely affected in proportion to the slowness of the rise and fall times of the modulated data signal. A low Q resonant circuit, e.g., a resonant circuit having a Q of four or less, would permit much sharper (faster) rise and fall times of the data signal.

Thus, it is seen that competing design goals are present. On the one hand, a high Q resonant circuit is needed in order to efficiently couple energy into the implant device. On the other hand, a low Q resonant circuit is needed in order to permit a more reliable data transfer into the implant device. The present invention advantageously addresses these competing design goals by providing a modulation amplifier in the external transmitter (used in the external charger 12 or the external control unit 14) that selectively alters the Q of the resonant circuit (which resonant circuit includes the primary coil and the implanted coil) as a function of whether the carrier signal is being modulated with data or not. Representative modulation amplifiers that may be used for this purpose are illustrated in FIGS. 4A and 4B.

Figure 4A:
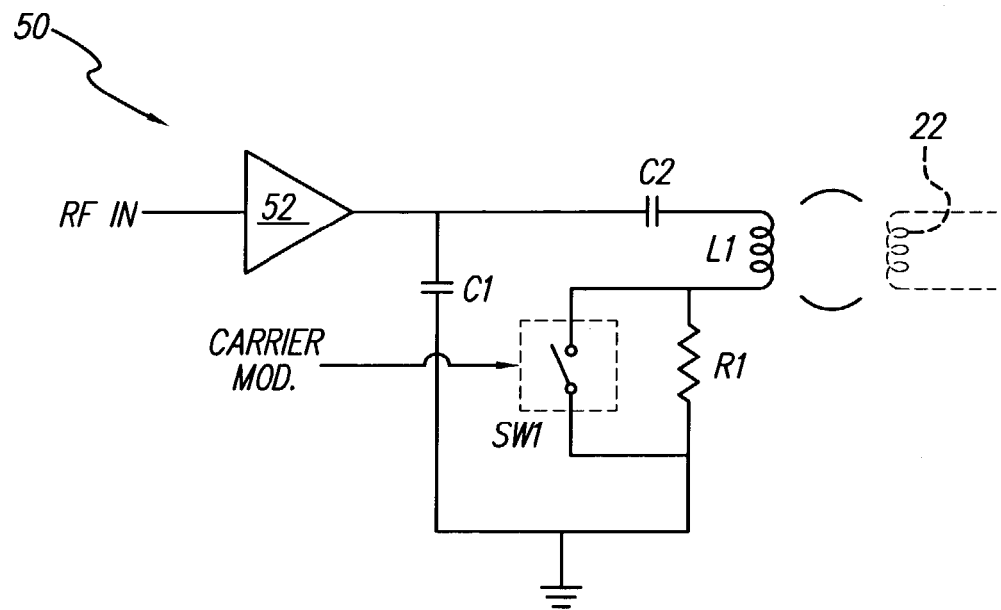
FIG. 4A illustrates one embodiment of the circuitry used in the external transmitter in order to implement the present invention.

As seen in FIG. 4A, a modulation amplifier 50 includes a suitable RF amplifier 52 that drives an LC circuit comprising a coil L1, a first capacitor C1 in parallel with the coil L1, and a second capacitor C2 in series with the coil L1. The capacitor C2 typically functions as a coupling capacitor. In operation, an implanted coil 22 (included as part of the implantable device 20) is inductively coupled with the coil L1. Hence, the combined inductance of the coil L1 coupled with the coil 22 determines the inductive reactance of the circuit. A switch SW1 selectively switches a resistor R1 in or out of circuit relationship with the coil L1. When SW1 is closed, the resistor R1 is effectively shorted out of the circuit. When SW1 is open, the resistor R1 is placed in series with the coil L1. The switch SW1 is controlled by a data-modulation-present signal that indicates when the carrier signal is being modulated with data. The data-modulation-present signal causes the switch SW1 to close, and hence removes the resistance R1 from the circuit, when the carrier signal is not modulated with data, i.e., at those times when a high Q resonant circuit would be beneficial for efficient energy coupling. The data-modulation-present signal causes the switch SW1 to open, and hence places the resistance R1 in series with the coil L1, when the carrier signal is modulated with data, i.e., at those times when a lower Q resonant circuit would be beneficial in order to allow shorter (faster) rise and fall times of the data modulation signal, thereby providing a more reliable data transfer.

Figure 4B:
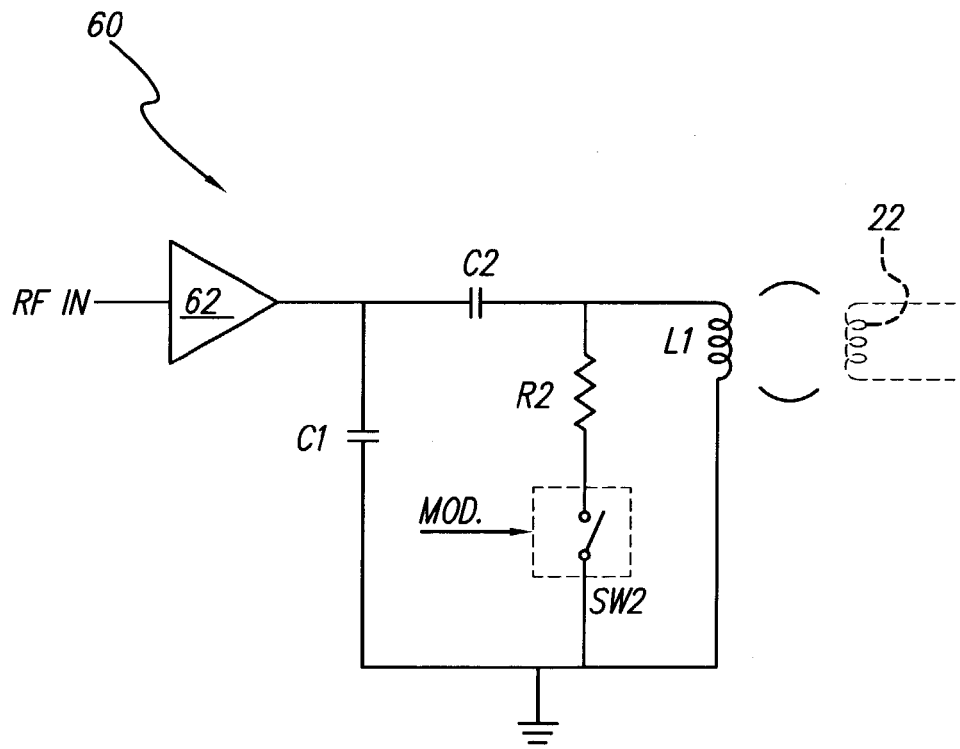
FIG. 4B shows an alternative embodiment of the circuitry of FIG. 4A.

An alternative modulation amplifier 60, shown in FIG. 4B, includes a suitable RF amplifier 62 that drives an LC circuit comprising a coil L1, a first capacitor C1 in parallel with the coil L1, and a second capacitor C2 in series with the coil L1. As with the modulation amplifier 50 of FIG. 4A, the capacitor C2 typically functions as a coupling capacitor. In operation, the implanted coil 22 (included as part of the implantable device 20) is inductively coupled with the coil L1. Hence, the combined inductance of the coil L1 coupled with the coil 22 determines the inductive reactance of the circuit. A switch SW2 selectively switches a resistor R2 in or out of circuit relationship with the coil L1. When SW2 is closed, the resistor R2 is effectively connected in parallel with the coil L1. When SW2 is open, the resistor R2 is removed from the circuit. The switch SW2 is controlled by a data-modulation-present signal that indicates when the carrier signal is being modulated with data. The data-modulation-present signal causes the switch SW2 to open, and hence removes the resistance R2 from the circuit, when the carrier signal is not modulated with data, i.e., at those times when a high Q resonant circuit would be beneficial for efficient energy coupling. The data-modulation-present signal causes the switch SW2 to close, and hence places the resistance R2 in parallel with the coil L1, when the carrier signal is modulated with data, i.e., at those times when a lower Q resonant circuit would be beneficial in order to allow shorter (faster) rise and fall times of the data modulation signal, thereby providing a more reliable data transfer.

The RF amplifier 52 (FIG. 4A) and/or the RF amplifier 62 (FIG. 4B) comprises a Class E amplifier, as is known in the art. The principle advantage of using a Class E amplifier is its low number of components and low power consumption. Other types of RF amplifiers, could of course, also be used, if desired.

Figure 5:
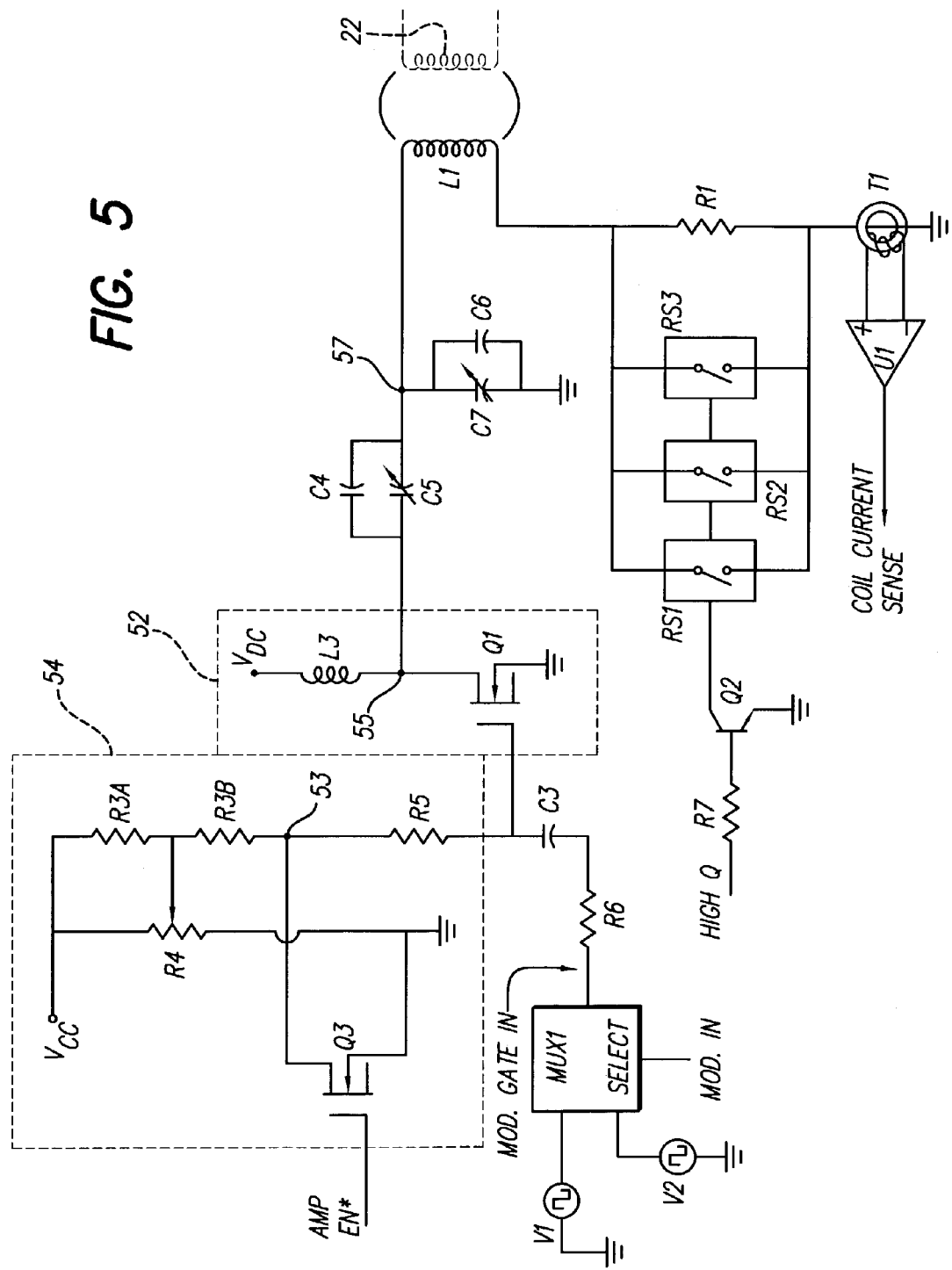
FIG. 5 shows a representative schematic implementation of the circuitry of FIG. 4A.

Turning next to FIG. 5, a schematic diagram of a preferred implementation of the circuitry of FIG. 4A is depicted. A modulated gate signal, MOD. GATE IN, is coupled to drive a Class E amplifier 52. The Class E amplifier includes a first FET transistor Q1 having its drain terminal connected to ground, and its source terminal connected to a coil L3 to a dc voltage, $V_{DC}$. The MOD. GATE IN signal is coupled to the gate terminal of the transistor Q1 through a resistor R6 and coupling capacitor C3.

The MOD GATE IN signal has a frequency $f_0$, or a period of $1/f_0$ and an amplitude V1 or V2, as determinated by a modulation signal, MOD. IN, applied to a multiplexer circuit, MUX1. The two inputs applied to the multiplexer circuit MUX1 include a signal having a frequency $f_0$ and an amplitude V1, or a signal having a frequency $f_0$ and an amplitude V2. When the MOD. IN signal assumes one value, e.g., a logical high or "true" value, the $f_0$ signal having amplitude V1 is selected as the modulated gate signal. When the MOD. IN signal assumes another value, e.g., a logical low or "false" value, the $f_0$ signal having amplitude V2 is selected as the modulated gate signal.

The gate terminal of the transistor Q1 is further connected to a bias circuit 54 that includes a bias resistor network made up of resistors R3A, R3B, R4 (a variable transistor), R5 and FET transistor switch Q3. Resistors R3A, R3B and R5 are connected in series between voltage source $V_{CC}$ and the gate of transistor Q1. Variable resistor R4 has its fixed resistance value connected between VCC and ground, and its wiper terminal connected to the node between resistors R3A and R3B. Hence, adjustment of the variable resistor R4 alters the bias current delivered to the gate of transistor Q1, which varies the amount of modulation present in the output signal of the amplifier 52. Transistor switch Q3 shunts circuit node 53 between resistor R3B and R5 to ground. An enable signal, AMP EN*, turns transistor Q3 on and off. This action, in turn, changes the gate current delivered to the base of transistor Q1 to turn the bias circuit 54 on or off. When the bias circuit 54 is turned on, the MOD GATE IN signal modulates the amplitude of the output signal, at node 55, by a prescribed amount, e.g., 20%. The amount of modulation present in the output signal may be adjusted, as desired by the variable resistor R4.

The output node 55 of amplifier 52 is connected through parallel capacitor network C4/C5 to output node 57. Another parallel capacitor network C6/C7 is connected between node 57 and ground. Capacitors C5 and C7 are preferably variable capacitors that can be adjusted. The parallel capacitor networks C4/C5 and C6/C7 allow the capacitance value presented by the capacitor networks to be adjusted, as required, through adjustment of the variable capacitors C5 and C7, as the resonant circuit (made up of coils L3 and L1 and implanted coil 22, and capacitance networks C4/C5 and C6/C7 is tuned to the desired resonant frequency.

As seen in FIG. 5, one side of the primary coil L1 is connected to output node 57. The other side of the primary coil L1 is connected in series with resistor R1 to ground through toroid transformer T1. Three relay switches, RS1, RS2, and RS3 are connected in parallel across the resistor R1. The switch contacts of these relay switches are opened when a HIGH Q drive signal is applied to turn transistor switch Q2 on. When transistor switch Q2 is off, the switch contacts of the parallel relays RS1, RS2 and RS3 are closed, which closure bypasses or shorts resistor R1, thereby effectively removing resistor R1 from the resonant circuit.

Implementation of the relay switches RS1, RS2 and RS3 may take various forms. In one embodiment, the relay switches RS1, RS2 and RS3 comprise solid state relays. In another embodiment, RS1, RS2 and RS3 comprise electromechanical relays. In yet other embodiments, the switches RS1, RS2, and RS3 may be made from one or more JFET's, two complementary MOSFET's in series, or a thyristor device. In still further embodiments, the function of the switches RS1, RS2, and RS3 (which function is to selectively switch the resistor R1 in or out of the circuit with coil L1) may be realized using one, two, three, four, or more separate switches, which switches may be solid state relays, electromechanical relays, JFET (junction field effect transistor) switches, MOSFET (metal oxide silicon field effect transistor) switches, or thyristor device switches, or any other suitable type switch. Indeed, any device which performs the function of a switch may be employed for the purpose of selectively switching the resistor R1 in or out of circuit relationship with the coil L1.

Three switches RS1, RS2, and RS3 are employed, in the preferred embodiment, to add redundancy, and to provide multiple current paths that may bypass the resistor R1. One switch, of course, could provide this same function of removing resistor R1 from the circuit. However, for this removal purpose, the applicants have determined that three switches are better than one, and allow the resonant circuit (that includes the antenna coil L1) to be de-tuned more rapidly. This is due, at least in part, to the fact that three switches in parallel, as shown in FIG. 5, provide a lower impedance shunt path around resistor R1 than would a single switch.

Still with reference to FIG. 5, toroid transformer T1 senses the current flowing through coil L1. The transformer T1 is connected to amplifier U1 to provide a coil current sense signal. This coil current sense signal may be used, as desired, to provide feedback and other useful information, e.g., reflected impedance to ascertain when the primary coil L1 is properly aligned with the implanted coil 22, or for other purposes associated with the operation of the implantable device system. The current flowing through coil L1 will vary significantly as a function of whether resistor R1 is switched into the circuit or not.

In one implementation of the invention shown in FIG. 5, voltage source $V_{DC}$ has a value of 12 volts, the coil L3 has a value of about 100 pH and the antenna coil L1 has a value of about 50 pH. The resistor R1 has a value of about 5 ohms. The capacitor C4 has a value of 100 pF, and the capacitor C5 may be varied between about 1.5 pF and 55 pF. Similarly, the capacitor C6 has a value of about 100 pF, and the capacitor C7 may be varied between about 1.5 pF and 55 pF.

In operation, the carrier signal having frequency $f_0$ is typically modulated with data at a very low duty cycle, e.g., a duty cycle of 4% or less, and preferably only about 2% or less, e.g., 1%. That means that, in a typical operation, resistor R1 is connected to coil L1 only about 4% of the time, or less.

As described above, it is thus seen that the present invention provides an external transmitter power amplifier circuit adapted to drive a primary coil that is inductively coupled with an implanted coil 22 associated with an implantable medical device, e.g., an implantable neural stimulator. For efficient power consumption, the transmitter output circuit (which includes the primary coil L1 driven by the power amplifier inductively coupled with the implanted coil 22) operates as a tuned resonant circuit. When operating as a tuned resonant circuit, it is difficult to modulate the carrier signal with data having sharp rise and fall times without using a high power modulation amplifier. Sharp rise and fall times are needed in order to ensure reliable data transmission. To overcome this difficulty, the present invention advantageously includes an output switch that selectively inserts a resistor R1 in the transmitter output coil circuit in order to de-tune the resonant circuit only during those times when data modulation is needed. Such de-tuning allows sharp rise and fall times in the data modulation without the need for using a high power modulation amplifier. Because data modulation is typically needed for only a small percent of the time that a carrier signal is present, it is thus possible using the present invention to achieve reliable data modulation, transmission and reception without having to use a high power modulation amplifier in the transmitter.

While the invention herein disclosed has been described by means of specific embodiments and applications thereof, numerous modifications and variations could be made thereto by those skilled in the art without departing from the scope of the invention set forth in the claims.

What is claimed is:

1. A low power modulation amplifier circuit adapted to be coupled with an implantable device, comprising:
    an amplifier having an output port through which a carrier signal is presented to a load, the load including an implantable coil associated with the implantable device;
    a first capacitance connected between the output port of the amplifier and a voltage reference;
    an antenna coil connected to the output port of the amplifier, the antenna coil comprising part of the load to which the carrier signal is presented by the amplifier;
    a resistor connected to the antenna coil; and
    a switch that switchably connects the resistor in circuit relationship with the antenna coil.

2. The amplifier circuit of claim 1 wherein the resistor is connected in series with the antenna coil when the switch is opened.

3. The amplifier circuit of claim 1 wherein the resistor is connected in parallel with the antenna coil when the switch is closed.

4. The amplifier circuit of claim 1 wherein the antenna coil forms part of a resonant circuit; and wherein the switch, when connected to the antenna coil, de-tunes the resonant circuit so that the resonant circuit has a Q of four or less.

5. The amplifier circuit of claim 4 wherein the carrier signal is modulated at a low duty cycle of no greater than about 4 percent.

6. The amplifier circuit of claim 5 wherein the carrier signal is modulated at a low duty cycle of no greater than about 2 percent.

7. The amplifier circuit of claim 1 wherein the switch comprises a plurality of switches connected in parallel.

* * * * *